(12) United States Patent
Sharma et al.

(10) Patent No.: US 12,239,676 B2
(45) Date of Patent: Mar. 4, 2025

(54) SYNBIOTIC COMPOSITION FOR IMPROVING IMMUNE RESPONSE AND ANTIOXIDANT CAPACITY DURING AGING AND A PROCESS FOR THE PREPARATION THEREOF

(71) Applicant: COUNCIL OF SCIENTIFIC & INDUSTRIAL RESEARCH, New Delhi (IN)

(72) Inventors: Rohit Sharma, Pradesh (IN); Mahesh Gupta, Pradesh (IN); Madhu Kumari, Pradesh (IM); Ashu Gulati, Pradesh (IN); Yogendra S. Padwad, Pradesh (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 18/219,581

(22) Filed: Jul. 7, 2023

(65) Prior Publication Data

US 2023/0346860 A1 Nov. 2, 2023

Related U.S. Application Data

(62) Division of application No. 17/260,052, filed as application No. PCT/IN2019/050515 on Jul. 11, 2019, now abandoned.

(30) Foreign Application Priority Data

Jul. 13, 2018 (IN) .............................. 201811026239

(51) Int. Cl.
 | | |
 |---|---|
 | *A61K 35/747* | (2015.01) |
 | *A61K 36/82* | (2006.01) |
 | *C12N 1/20* | (2006.01) |
 | *C12R 1/225* | (2006.01) |

(52) U.S. Cl.
CPC ............ *A61K 35/747* (2013.01); *A61K 36/82* (2013.01); *C12N 1/20* (2013.01); *C12R 2001/225* (2021.05)

(58) Field of Classification Search
CPC .... A61K 35/747; A61K 36/82; A61K 31/353; A61K 2035/115; A61K 2300/00; C12N 1/20; C12R 2001/225; A23L 33/105; A23L 33/135; A23L 33/21
See application file for complete search history.

(56) References Cited

U.S. PATENT DOCUMENTS

| | | | |
|---|---|---|---|
| 8,927,252 B2 | 1/2015 | Wadstrom et al. | |
| 9,771,624 B2 | 9/2017 | Van Sinderen et al. | |
| 2003/0099730 A1 | 5/2003 | Rosenbloom | |
| 2009/0022852 A1 | 1/2009 | Simmons et al. | |
| 2015/0118267 A1 | 4/2015 | Li et al. | |
| 2015/0313952 A1 | 11/2015 | Wang et al. | |
| 2015/0366919 A1 | 12/2015 | Garssen et al. | |

FOREIGN PATENT DOCUMENTS

| | | |
|---|---|---|
| EP | 1600061 B1 | 5/2010 |
| KR | 20080107847 A | 12/2008 |
| WO | 9910476 A1 | 3/1999 |
| WO | 0115714 A1 | 3/2001 |
| WO | 02060276 A8 | 10/2003 |
| WO | 2004032639 A1 | 4/2004 |
| WO | 2006048457 A1 | 5/2006 |
| WO | 2012178118 A1 | 12/2012 |
| WO | 2014165975 A1 | 10/2014 |

OTHER PUBLICATIONS

Sharma, R et al. Diet supplemented with phytochemical epigallocatechin gallate and probiotic Lactobacillus fermentum confers second generation synbiotic effects by modulating cellular immune responses and antioxidant capacity in aging mice. European Journal of Nutrition. 2019. 58: 2943-2957. (Year: 2019).*
A. Sourabh, et al., "Influence of phenolic compounds of Kangra tea [*Camellia sinensis* (L)O Kuntze] on bacterial pathogens and indigenous bacterial probiotics of Western Himalayas," Brazilian Journal of Microbiology, vol. 44, No. 3, pp. 709-715 (2013).
H. C. Lee, et al., "Effect of tea phenolics and their aromatic fecal bacterial metabolites on intestinal microbiota," Research in Microbiology, vol. 157, ppl. 876 884 (2006).
J. A. Krumbeck, et al., "Prebiotics and synbiotics: Dietary strategies for improving gut health," Current Opinion in Gastroenterology, vol. 32, pp. 110-119 (2016).
Kumari, Met al. Genome sequence of a potential probiotic strain, Lactobacillus fermentum HFB3, isolated from a human gut. Genome Announcements. 2015. 3(6): e01296-15. 2 pages. (Year: 2015).
R. Sharma, et al., "Consumption of green tea epigallocatechin-3-gallate enhances systemic immune response, antioxidative capacity and HPA axis functions in aged male swiss albino mice," Biogerontology, vol. 18, pp. 367-382 2017).
Sourabh, A et al. Influence of phenolic compounds of Kangra tea [*Camellia sinensis* (L) O Kuntze] on bacterial pathogens and indigenous bacterial probiotics of Western Himalayas. Brazilian Journal of Microbiology. 2013. 44(3): 709-715. (Year: 2013).

\* cited by examiner

*Primary Examiner* — David W Berke-Schlessel
*Assistant Examiner* — Susan E. Fernandez
(74) *Attorney, Agent, or Firm* — Blank Rome LLP (57) ABSTRACT

The present invention provides a symbiotic combination of i) a probiotic micro-organism comprising of a *Lactobacillus* strain, and ii) a catechin component comprising EGCG that acts as a second generation symbiotic with synergistic effects in improving the immune response and antioxidant capacity during aging that may beneficially affect the health of elderly.

9 Claims, 11 Drawing Sheets

SYNBIOTIC COMPOSITION FOR IMPROVING IMMUNE RESPONSE AND ANTIOXIDANT CAPACITY DURING AGING AND A PROCESS FOR THE PREPARATION THEREOF

RELATED APPLICATIONS

The present application is a divisional application of U.S. national phase application Ser. No. 17/260,052, filed 2021 Jan. 13 under 35 USC § 371 of PCT/IN2019/050515, filed on 2019 Jul. 11, which claims the benefit of IN 201811026239, filed 2018 Jul. 13, the disclosures of which are hereby incorporated by reference in their entireties.

FIELD OF THE INVENTION

The present invention relates to a synbiotic composition for improving immune response and antioxidant capacity during aging and a process for the preparation thereof. In particular, the present invention relates to a second generation synbiotic composition for use in enhancing immune response and oxidative homeostasis during aging, comprising a novel combination of probiotic *Lactobacillus fermentum* and the phytochemical epigallocatechin gallate. The developed composition was analyzed for several immunological parameters including lymphocyte sub-populations, lymphocyte activations status, innate immune cells functions and inflamm-aging in organs while antioxidant capacity was analyzed both in tissues and systemic circulation. It was observed that the synbiotic composition is immensely useful as an effective immune and antioxidant rejuvenator that would resist infections and maintain robust homodynamic systems thereby improving the quality of life in elderly. This patent documents the first comprehensive report highlighting the applicability of cost-effective and highly efficacious health beneficial aspects of nutraceuticals and probiotic bacteria combination during aging which influence gut microbiota in a way that renders health beneficial effects on the host.

BACKGROUND OF THE INVENTION AND DESCRIPTION OF PRIOR ART

Human aging is a complex, extremely heterogeneous and dynamic trait determined by a number of environmental, genetic, epigenetic, and stochastic factors. In particular, several characteristic age-associated changes in regulatory systems of the body, including immune system (immunosenescence) and antioxidant capacity have been documented. Together, immunosenescence and oxidative stress constitute a grave threat for the rationale of 'healthy aging' and pose a challenge to public health systems worldwide. In fact, an increased emphasis is attributed to the development of food and nutrition based strategies for amelioration of age-associated changes in immunity and redox homeostasis. In this regard, several reports have established that probiotic bacteria can modulate a variety of regulatory functions in humans including immune response, gut health and even neuro-endocrine systems.

The term "probiotic" is defined as live micro-organisms that, when administered in adequate amounts, confer health benefits to the host (FAO/WHO guidelines). This generally includes bacteria of *Lactobacillus* and *Bifidobacterium* genera with their potential health beneficial effects being very species and strain specific. A "Prebiotic" has traditionally been defined as compounds, usually oligosaccharides that cannot be digested by enzymes of the upper gastro-intestinal tract but are fermented by some types of intestinal bacteria in the colon, or large intestine. A "synbiotic" is the synergistic combination of a probiotic component and a prebiotic component. A synergy can be observed when the combined effect of two treatments, components, or ingredients, is different from the purely additive effect that can be expected from each treatment, component, or ingredient taken separately. Usually, the effect of the combination is greater than the added effect of each treatment, component, or ingredient taken separately. However, the mix of a prebiotic and a probiotic is not always a synbiotic and is greatly influenced by not only the type of prebiotic but also by the species and strain of bacteria employed. This is the case when no synergistic effect is observed.

Reference may be made to U.S. Pat. No. 8,927,252 B2 which describes the use of symbiotic compositions comprising probiotic bacterial strains and prebiotic substances to stimulate the indigenous micro flora to restore and reconstitute in vivo gut like conditions after intestinal disorders. The prebiotic component belongs to either resistant starch or soluble starch. However, the drawbacks associated with this prior art is that starch has been used as source of prebiotics, as opposed to catechin EGCG used in present invention which has shown evidence of synergistic effects and thus superior health beneficial attributes.

Reference may be made to US 20150313952 A1 that relates to the use of arabino-xylo-oligosaccharides as prebiotic substances for the growth of probiotic bacteria and maintenance of healthy gut environment. However, this prior art shows use of oligosaccharides as prebiotics while the present invention claims that tea polyphenols are not only source of prebiotics, but also confer health beneficial attributes in conjunction with specific probiotic bacteria.

Similarly, reference may be made to US 20150366919 A1 which describes the use of non-digestible oligosaccharides as prebiotics to be used as synbiotics for use in improving cognitive or behavioral performance. However, this prior art uses oligosaccharides as source of prebiotics which have little or no functional efficacy on their own. The present invention reveals that tea phenol is not only a source of prebiotics, but its combination with specific probiotic bacteria is also a capable source of immunomodulation during aging.

Reference may be made to WO 2002060276 A1 which discloses a preparation having immune stimulatory and general health improvement functions, containing one or more probiotics and one or more non-digestible oligosaccharides. The probiotics were chosen from strains of *Lactobacillus*, *Bifidobacterium*, or *Propionibacterium*. However, the drawbacks associated with this prior art is that no specific age-associated immune dysfunctions have been tested and that the results are general in nature. Besides, non-digestible oligosaccharides have been used as source of prebiotics as opposed to tea catechin in present invention.

Reference may be made to WO 2001015714 A1 which discloses a composition comprising micronutrients along with prebiotics, probiotics, and/or synbiotics for enhancing general immunity. The prebiotic selected is from at least one member of the group consisting of FOS, inulin, GOS, lactulose, and lactitol. This prior art again emphasizes that insoluble oligos have been used as prebiotics for developing nutraceutical formulation as modulators of immunity while in present invention, a more superior nutraceutical, i.e. EGCG, has shown potential as a prebiotic with specific effects on cellular immune responses during aging.

Reference may be made to WO 2004032639 A1 which discloses a nutritional composition comprising of oligofructose, sialyllactose and probiotic bacteria, which are useful in the eradication of pathogenic microorganisms in the gastrointestinal tracts of patients. However, the drawbacks associated with this prior art is that use of oligosaccharides as sources of prebiotics is not as efficacious as phenols such as EGCG used in present invention, which has also shown ability to modulate cellular immune responses.

The conventional prebiotics such as non-digestible carbohydrates greatly enhance the growth of probiotics but they are also liable to encourage growth of non-probiotic bacteria such as *Eubacterium* or *Clostridium* sp. Therefore, it is desirable to identify non-carbohydrate alternatives of prebiotics with ability to differentially modulate bacterial growth in a way that confers health beneficial effects. These may include bioactive molecules of plant origin such as polyphenols, anthocyanins etc. which have known bioactive attributes. It is also pertinent to note that emerging evidences have suggested that prebiotics could be best defined based on their physiological effects or functional capacities in host rather than their specific microbial targets, as often viewed conventionally (Krumbeck et al. 2016). These, so called 'second generation synbiotics' thus confer specific health beneficial effects on host rather than simply modulating gut microbiome or related effects. Catechins are natural antioxidant plant secondary metabolites belonging to the chemical family of flavonoids that are widely reported to possess several health beneficial attributes.

With respect to influence on bacterial growth, catechins have been generally considered as anti-bacterial agents but some studies have also reported that catechins can differentially modulate bacterial growth with a greater inhibitory influence on pathogenic bacteria as opposed to probiotic bacteria (Lee et al. 2006; Sourabh et al. 2014). Reference may be made to EP 1600061 A1 which describes the use of plant polyphenols as prebiotics for stimulating growth of several probiotic bacteria. However, the drawbacks associated with this prior art is that it only reveled that plant phenols could favorably modulate growth of probiotic bacteria but it did not ascertain health beneficial effects of an identified synbiotic combination on regulatory system of the body, such as immune responses as otherwise tested in present invention.

Reference may be made to US 20090022852 which describes a liquid composition of a non-digestible oligosaccharide, at least one green tea catechin, at least one antioxidant comprising ascorbic acid and a buffering agent for improving colon health and function. However, the drawbacks associated with this prior art is that while it has shown that phenols could be components for improving colon heath; it did not ascertain the effects of a proven synbiotic composition for improving health during aging that is different from simple modulation of gut microbiota.

Reference may be made to WO 2014165975 A1 that describes the combination of epigallocatechin gallate and non-digestible oligosaccharides to prevent and/or treat one or more gastrointestinal imbalances associated with digestive disorders. However, the drawbacks associated with this prior art is that while it describes how epigallocatechin gallate could be useful in prevention of digestive disorders; it did not use any specific and compatible probiotic bacteria for further testing of its efficacy on general helath especially during aging.

The synergistic combination of probiotic bacteria and tea catechins have not been utilized as synbiotics for improving health in elderly. US 20150118267 describes the use of tea theaflavins and catechins in enhancing immunity and treating infectious diseases. WO 2012178118 describes the use of combination of various bioactive components including EGCG in enhancing or suppressing immune responses. WO 9910476 relates use of probiotic *Lactobacillus* and *Bifidobacterium* sp in stimulating immune response in healthy animals. U.S. Pat. No. 9,771,624 describes the use of *Bifidobacterium* sp as probiotics and immunomodulators in treatment of inflammation. The use of bioactive components catechins as prebiotic for probiotic bacteria, so as to generate an elderly specific second generation synbiotic product has not been reported as traditionally catechins have been considered as anti-microbial that may be lethal to probiotic bacteria.

The prior art discussed above discloses synbiotic formulations of proven health beneficial aspects using conventional non-digestible oligosaccharides-based prebiotics only. The use of polyphenols as synbiotics have only been suggested for improvement of gut health or microbiome and associated conditions with no specific health benefits. Further, the prior art lacks any synbiotic product specifically aimed at boosting the health of elderly. In this regard, it is worth mentioning that aging physiology shows distinct characteristics in several regulatory systems of the body, both in terms of functions and specificity, thereby necessitating the use of aging systems for development of any potential anti-aging strategies. Overall, the prior art has failed to provide an alternative prebiotic (such as flavonoids) based anti-immunosenescence, antioxidant and anti-inflamm-aging synbiotic combination for elderly that may help boost immunity, redox homeostasis and ultimately improve quality of life in elderly.

Traditional synbiotics are combinations of prebiotics and probiotics which influence gut microbiota in a way that renders health beneficial effects on host. Thus, the health benefits of known synbiotic combinations are limited to improving the gut microbiome, strengthening the gut mucosal barrier and resisting pathogen colonization in gut. These synbiotic preparations suffer a disadvantage of lack of documented systemic effects on regulatory systems of the body such as immune system. Our developed synbiotic composition is of second generation that shows multiple health beneficial synergistic effects in both immune and redox functions in vivo.

The global health care market for elderly is expected to grow exponentially due to the ever-increasing aging population. Due to high costs and potential side-effects, a particular emphasis is focused on developing food- and nutrition-based strategies to rejuvenate the aging immune system as an attempt to ultimately boost immunity, antioxidant capacity, and augment healthy aging. Therefore, the present invention proposes a novel combination of catechins and probiotics that can render synergistic health beneficial effects on aging physiology Thus, keeping in view the drawbacks of the hitherto reported prior art, the inventors of the present invention attempted to solve the aforementioned problems by testing known plant polyphenols as prebiotics followed by further assessment of their specific synbiotic attributes with probiotic bacteria of *Lactobacilli* origin using in vitro as well as in vivo approaches. In this regard, a unique synbiotic combination of tea catechins and probiotic bacteria was developed with potential to rejuvenate immunity and anti-oxidative functions in elderly with an aim to raise their quality of life and coming up with an effective solution to their problems. This is thus a preventive as well as rejuvenating approach that will maintain robust immune response and resist infections thereby improving the socio-economic landscape.

OBJECTIVES OF THE INVENTION

The main objective of the present invention is therefore to provide a unique synbiotic composition wherein both components possess bioactive properties resulting in several synergistic effects on regulatory systems of the host body.

Another objective of the present invention is to provide a synergistic combination of probiotic bacteria and green tea epigallocatechin gallate (EGCG) useful for the alleviation of age-associated cellular stresses and oxi-inflamm-aging and improving immune responses.

Still another objective of the present invention is to provide a synbiotic composition that mitigates inflammatory and oxidative stress both in vitro and in vivo signifying that the combination has age-associated stress ameliorating synergistic effects that could greatly impact cell functions during aging.

Yet another objective of the present invention is to provide a synbiotic composition that provides total catechins equivalent to drinking 4-5 cups of green tea in albeit a single drink/formulation that would be suitable for people who resent green tea due to its native astringent taste.

Still another objective of the present invention is to provide a synbiotic composition that significantly influences the cellular immune response with increased numbers as well as activation status of CD3+ T cells that could help mitigate recurring infections in elderly.

Yet another objective of the present invention is to provide a synbiotic composition wherein the synergy of catechins and probiotic *Lactobacilli* enhances functional capacity of immune cells with a strong increase in Th1/Th2 cytokines production along with enhanced neutrophils respiratory burst suggesting robust immune activity in wake of either infection or allergic response.

Still another objective of the present invention is to provide a synbiotic composition having synergy of catechins with probiotic *Lactobacilli* which beneficially alters the gut microbiome as catechins differentially influence bacterial growth.

SUMMARY OF THE INVENTION

The present invention proposes a novel synergistic combination of probiotic *Lactobacillus fermentum* and the prebiotic epigallocatechin gallate for improving immune response and antioxidant capacity during aging and a process for the preparation thereof. The essential process steps involve isolation and characterization of phytochemical epigallocatechin gallate from tea leaves; culture and maintenance of probiotic *Lactobacillus fermentum*; mixing of epigallocatechin gallate with *Lactobacillus fermentum* in a particular concentration to obtain the desired synbiotic composition.

In an embodiment, the process of the present invention involves identification of particular species of probiotic bacteria that confers health beneficial effects in combination with phytochemical epigallocatechin gallate and identification of the particular physiologically relevant concentration of epigallocatechin gallate that confers desired health beneficial effects along with the identification of physiological phenomenon which are synergistically affected on consumption of the developed synbiotic combination during aging.

In another embodiment, the present invention provides a combination of i) a probiotic micro-organism comprising a *Lactobacillus* strain, and (ii) a green tea catechin, epigallocatechin gallate (EGCG) having synergistic effect on cellular immune response and antioxidative capacity during aging in a way that renders beneficial effects on aging physiology. Therefore, the invention proposes a second generation synbiotic functional food product(s) comprising this synbiotic composition, for improving immunity and redox homeostasis in elderly thereby promoting the concept of 'Healthy Aging'.

In still another embodiment of the present invention, epigallocatechin gallate (EGCG), isolated from *Kangra* green tea leaves (*Camellia sinensis*), was screened in combination with different probiotic *Lactobacillus* sp. for amelioration of various cellular stressors so as to identify a second generation synbiotic preparation. The present invention reports for the first time the usage of combination of tea catechins and a probiotic bacterium with specific immunological and antioxidative health beneficial effects on aging physiology that may augment health of elderly. The identified combination of EGCG and probiotic bacteria showed immunomodulatory as well as antioxidant attributes both in vitro and in vivo that augmented cell survival and function under age-associated inflammatory and oxidative stress. The synbiotic combination was analyzed for several immunological parameters including lymphocyte sub-populations, lymphocyte activations status, innate immune cells functions and inflamm-aging in organs while antioxidant capacity was analyzed both in tissues and systemic circulation.

In yet another embodiment of the present invention, the concentration of epigallocatechin gallate required is 400-500 mg for adult Human and CFU of probiotic bacteria required is $10^8$-$10^9$ CFU.

In still another embodiment, the present invention provides a second generation synbiotic composition, wherein the said composition comprising:
(i) a probiotic micro-organism selected from a *Lactobacilli* strain, and
(ii) a prebiotic epigallocatechin gallate [EGCG];
wherein the ratio of component (i):component (ii) ranges from 1:1 to 2:1.

In yet another embodiment of the present invention, the EGCG can be derived either synthetically or from a natural source.

In still another embodiment of the present invention, the epigallocatechin gallate (EGCG) is isolated from *Kangra* green tea leaves (*Camellia sinensis*).

In yet another embodiment of the present invention, the *Lactobacillus* strain is selected from *Lactobacillus fermentum* MCC 3160 and *Lactobacillus plantarum* MCC 3165.

In still another embodiment of the present invention, the *Lactobacillus* strain is *Lactobacillus fermentum* MCC 3160.

In yet another embodiment of the present invention, the composition is administered in the dosage ranging from 6.66 to 10 mg/kg body weight in the subject.

In still another embodiment of the present invention, the composition is useful for improving immune response and antioxidant capacity during aging.

In yet another embodiment of the present invention, the composition enhances immune response comprising modulation of cellular immune response with a general increase in numbers of CD3+ T cells, along with enhanced activation of CD3+ T cells and neutrophils as well as activation of both Th1 and Th2 immune systems.

In still another embodiment of the present invention, the enhancement of antioxidant capacity comprises activation of Nrf2 transcription factor resulting in robust antioxidant capacity and thus enhanced redox homeostasis during aging.

In yet another embodiment, the present invention provides a process for the preparation of the composition, wherein the steps comprising:

[a] preparing 1 to 10 micromolar solution of the prebiotic epigallocatechin gallate;

[b] culturing the probiotic *Lactobacillus* strain in MRS medium followed by incubation at 37 degree C. for 16 to 24 hours under shaking;

[c] mixing the epigallocatechin gallate solution obtained in step [a] with the *Lactobacillus* strain obtained in step [b] to obtain the desired synbiotic composition.

List of All the Abbreviations Used in the Invention

| | |
|---|---|
| EGCG | Epigallocatechin gallate |
| LF | *Lactobacillus fermentum* |
| LR | *Lactobacillus rhamnosus* |
| LP | *Lactobacillus planatarum* |
| tBHP | Tert-Butyl hydroperoxide |
| PBMCs | Peripheral blood mononuclear cells |
| CFU | Colony forming units |
| PRE | Prebiotic |
| PRO | Probiotic |
| SYN | Synbiotic |
| NK | Natural killer cells |
| NKT | Natural killer T cells |
| LPS | Lipopolysaccharide |

Details of Biological Resources Used in the Invention

The probiotic bacterial strain of *Lactobacillus fermentum* [MCC 3160] was isolated from human faeces obtained from Village Bundala Distt. Kangra, Himachal Pradesh and the bacterial strain of *Lactobacillus plantarum* [MCC 3165] was isolated from human faeces obtained from Village Kandi, Distt. Kangra, Himachal Pradesh. The two isolated bacterial strains *Lactobacillus fermentum* and *Lactobacillus plantarum* were identified and characterized; following which they were deposited in the microbial culture collection repository of National Centre of Cell Science, Pune, India vide accession number MCC 3160 and MCC 3165 respectively on 13 Jun. 2016. The bacterial strain of *Lactobacillus rhamnosus* ATCC 53103 was commercially procured from ATCC, USA.

The second component in the present study i.e. phytochemical epigallocatechin gallate was isolated and characterized from green tea leaves [*Camellia sinensis*] grown and maintained at Tea farm of CSIR-IHBT, Palampur, Himachal Pradesh, India.

DETAILED DESCRIPTION OF THE INVENTION

The present invention reports for the first time the combination of prebiotic epigallocatechin gallate (EGCG) and a probiotic bacterium with specific immunological and anti-oxidative health beneficial effects on aging physiology. The said combination offers synergistic health beneficial effects in improving immunity and antioxidant capacity during aging, while presenting an economically viable food product with advantages of both probiotics and catechins in improving health, especially of elderly.

The starting materials in present invention are probiotic *Lactobacillus fermentum* and green tea phytochemical epigallocatechin gallate. The probiotic bacteria was isolated, identified and characterized for probiotic attributes and then screened in combination with epigallocatechin gallate for ameliorating cellular stresses. The best identified combination has been tested and analyzed for health beneficial effects during aging. The concept of synbiotics essentially refers to a synergistic combination of probiotic bacteria with small biomolecules that together have a greater effect on probiotic bacterial population. Conventional synbiotics have been considered beneficial owing to their ability to stimulate probiotic bacterial growth ultimately resulting in establishment and/or maintenance of intestinal homeostasis. A more inclusive and effective approach called 'second generation synbiotic combination' has been recently defined that encourages specific health beneficial effects in hosts without necessarily influencing the microbial community per se.

The present invention proposes green tea catechins as prebiotic candidates in combination with probiotic *Lactobacillus* strain for development of novel second generation synbiotic aimed at imparting health beneficial effects in elderly. Using bioactive molecules, such as catechins, for a synbiotic preparation will offer additional advantage as the synergistic combination would have the ability to confer health benefits of catechins and probiotics as well as their mutual association.

In a first aspect of the invention, effects of EGCG on various bacterial species was profiled by examining the growth of different bacteria, including both pathogens and probiotics, in presence of EGCG. The co-existence of potential prebiotics with probiotic bacteria is a crucial aspect of the study following which the subsequent synergistic effects could be envisaged. The strong inhibition of growth of pathogenic bacteria with minimal effects on probiotic bacteria, on account of EGCG as observed in present study, could not only provide favorable environment for the growth of probiotics, but may also help reduce the occurrence as well as the severity of an infection. The probiotic bacteria used in present invention were isolated, identified and characterized from different regions of Himachal Pradesh. These probiotic bacteria have been deposited in Microbial culture collection repository of National Centre of Cell Science, Pune, India. A well-known probiotic *Lactobacillus rhamnosus* ATCC 53103 was used as a reference strain.

In a second aspect of the study, different combinations of EGCG [1 to 10 micromolar] and probiotic bacteria were assessed for synergistic effects using in vitro cultured cells. The protective synergistic effects of these combinations were tested against inflammatory and oxidative stress in peripheral blood mononuclear cells (PBMCs) of mice. A model of lipopolysaccharide induced inflammatory stress and tert-Butyl hydroperoxide (tBHP) induced oxidative stress respectively was established in PBMCs in vitro. The chosen stress types mimic the kind of environment cells usually face in an aging physiology. Several doses of EGCG were tested and the minimum dose with negligible cellular inhibition was selected for subsequent analysis. Probiotic bacterial culture (24 h old) supernatants were used for preparation of probiotic conditioned media that was subsequently used for in vitro testing. The best stress-ameliorating combination(s) of EGCG and probiotic bacterial species were identified by analyzing cell death and pro-inflammatory cytokines production. Chronic inflammatory and oxidative stress (oxi-inflamm-aging) is amongst the major contributor driving the aging process per se as well as immunosenescence and other allied pathologies.

In another aspect, the choice of synbiotic combination for further testing was exclusively based on their potential of ameliorating the cellular stressors in vitro which thus would have direct implication on aging physiology.

In yet another aspect, the EGCG component comprised of a concentration which is effective, physiologically achievable and practical for human consumption (Sharma et al. 2017).

In another aspect of the invention, the best identified synergistic combination was tested for its health beneficial effects in aging animals.

In still another aspect of the invention, male swiss albino mice at 16 months of age were selected for analysis based on our previous observations (Sharma et al. 2017). This particular age of animals is an ideal model for studying anti-aging or immunomodulatory effects as several characteristic age-associated changes in immunity as well as antioxidant capacity have been noted in these animals. The probiotic *Lactobacillus*, EGCG or a combination of the two were orally administered to aged animals for 31 days before sacrificing and subsequent analysis of various immune and oxidative stress associated parameters. The invention laid special emphasis on analyzing specific immunological and redox stress related effects of synbiotic treatment in comparison to individual treatment. This included immunophenotyping of major cell sub-populations in splenic cells, analysis of functional capacity of various immune cells, humoral immune response, inflamm-aging, and antioxidant capacity.

The synbiotic composition can be incorporated into a food composition, for instance by dry mixing the components of the synbiotic composition successively, together or as a premix, into a food composition, following regular processing techniques. Another strategy could be the incorporation of the synbiotic composition in a milk-based formulation which could be cost effective and tempting for general consumption. Optionally, the food product comprises added nutrients selected from minerals, vitamins, amino-acids, unsaturated fatty acids, polyphenols, plant sterols, and mixtures thereof. Preferably, the food composition is for use in improving immune response, alleviate oxidative and inflammatory stress, resist infections that would ultimately improve critical regulatory functions of the body thereby contributing to healthy aging.

The developed synbiotic composition is unique and is not obvious to a person skilled in art as is evident by the synergistic effects exerted thereby and illustrated in the examples and drawings accompanying the specification. Further, the protocols used to identify the claimed combination and test its in vivo efficacy in an animal species with known aging patterns, requires multiple layers of research and understanding that is not known to a person without disclosing the exact parameters. None of the hitherto reported prior arts motivate a person skilled in the art to arrive at such claimed combination of ingredients with the desired technical effects.

In an embodiment of the present invention, mixing of the epigallocatechin gallate solution with the *Lactobacillus* strain is done either after lyophilization of bacteria or directly by mixing bacteria or its culture supernatant metabolites with EGCG directly.

BRIEF DESCRIPTION OF THE ACCOMPANYING DRAWINGS

FIG. 1. Effect of EGCG on growth of probiotic and pathogenic bacterial species. The growth was monitored by inoculating a 5% inoculum of respective bacterial species into media containing 0.1% of EGCG. Growth was compared to that of control (without EGCG) to determine the influence of EGCG by spectrophotometric method (600 nm). *Lactobacillus rhamnosus* (LR); *Lactobacillus fermentum* (LF); *Lactobacillus planatarum* (LP); *Escherichia coli* (EC; MTCC 43); *Salmonella typhi* (ST; MTCC 733); *Pseudomonas aeruginosa* (PS; MTCC 424); *Staphylococcus aureus* (SA; MTCC 96); *Klebsiella pneumoniae* (K; MTCC 109); *Shigella flexneri* (SF; MTCC 1457); *Vibrio cholera* (VC; MTCC 3904).

FIG. 3. Effect of synbiotics on amelioration of LPS induced inflammatory stress in murine PBMCs. Cells were incubated with LPS (1 µg/ml) for 24 h in presence or absence of EGCG (1 µM) and probiotic bacteria supernatant (10%). Cell supernatants were collected and analyzed for (A) TNF-α (B) IL-6 and (C) IFN-γ by ELISA.

FIG. 4. Effect of synbiotics supplementation on T cells sub-population of aging animals. Animals were fed with respective diets for 31 days following which splenocytes were analyzed by flow cytometry. (A) % CD3+ cells (B) % NK cells and (C) % NKT cells. Bars with different letter indicate significant difference at $p<0.05$.

FIG. 5. Effect of synbiotics supplementation on activation status of T cells sub-population of aging animals. Animals were fed with respective diets for 31 days following which splenocytes were analyzed by flow cytometry. (A) Activated T cells (B) Activated NK cells and (C) Activated NKT cells. Bars with different letter indicate significant difference at $p<0.05$.

FIG. 6. Effect of synbiotic supplementation on (A) Oxidative index of neutrophils. Representative Flow cytometry plots of different treatments (B) Control (C) Prebiotic (D) Probiotic (E) Synbiotic. Bars with different letter indicate significant difference at $p<0.05$.

FIG. 7. Effect of synbiotic supplementation on Th1/Th2 immune homeostasis as measured by ELISA in splenocytes culture supernatant (A) TNF-α (B) IL-6 (C) IFN-γ and (D) IL-10. Bars with different letter indicate significant difference at $p<0.05$.

FIG. 10. Western blot analysis of effect of synbiotic supplementation on transcription factors (A) Nrf-2 and (B) Nfk-B in modulating antioxidant and inflammatory responses respectively in liver of aging animals.

EXAMPLES

The following examples are given by way of illustration only and therefore should not be construed to limit the scope of the present invention in any manner.

Example 1

Prebiotic Attributes of EGCG

Figure 1:
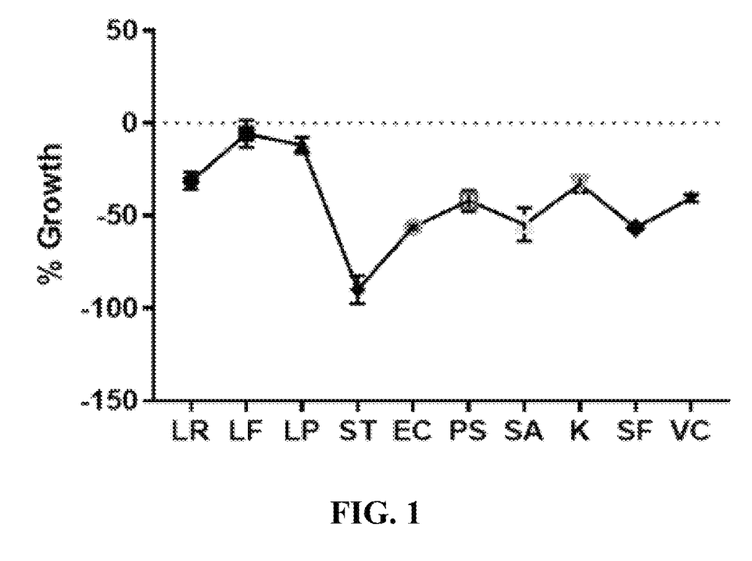

To test prebiotic efficacy, the effect of EGCG on growth of probiotic bacteria (*Lactobacillus* species) and pathogenic bacteria [*Escherichia coli* (EC); *Salmonella typhi* (ST); *Pseudomonas* (PS); *Staphylococcus aureus* (SA); *Klebsiella* (K); *Shigella flexneri* (SF); *Vibrio cholera* (VC)] was assessed. The probiotic bacteria were isolated, identified and characterized while the pathogenic bacteria were procured from MTCC, Chandigarh. It was observed that EGCG invariably inhibited bacterial growth of all species but the extent of inhibition varied significantly. On an average, a 14.05% (Max: 31%; Min: 1.4%) decrease in growth of probiotics was observed on account of EGCG supplementation while all pathogens recorded on average 52.05% (Max: 89.88%; Min: 32.7%) growth inhibition in presence of EGCG (FIG. 1). Thus, it was apparent that EGCG selectively inhibited bacterial growth with significantly greater inhibition of gram negative pathogenic bacteria implying that EGCG can change in the microbial milieu and favour growth of probiotics and thus could be a candidate prebiotic.

Example 2

In Vitro Synergistic Effects of the Synbiotic Composition

Figure 2:
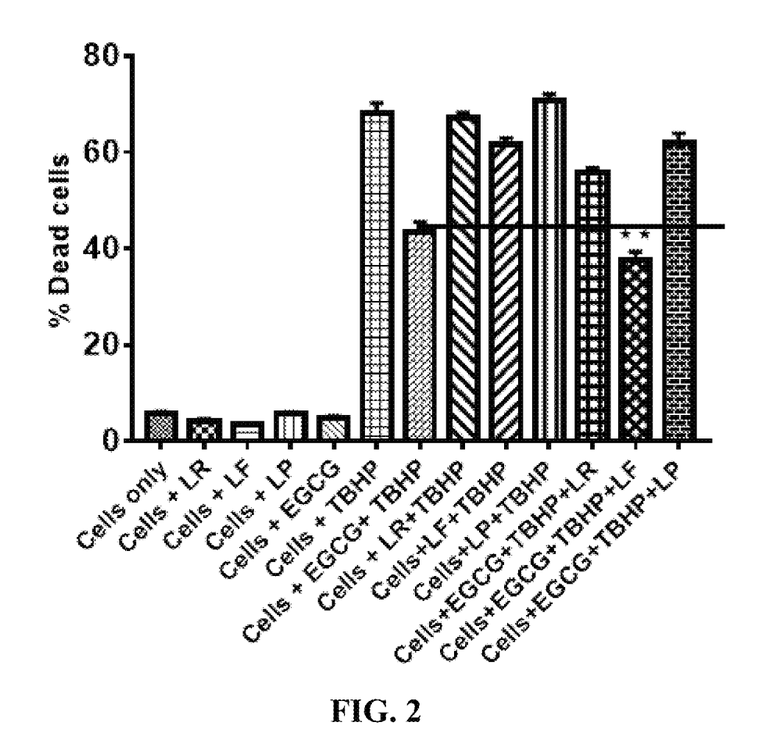
FIG. 2. Effect of synbiotics on amelioration of tBHP [cert-Butyl hydroperoxide] induced oxidative stress in murine PBMCs. Cells were incubated with tBHP (1 mM) for 3 h in presence or absence of EGCG (1 µM) and probiotic bacteria supernatant (10%). The percent dead cells were evaluated by Flow cytometry. Significant difference between the EGCG treated and synergistic group is indicated by an asterisk mark, ** ($p<0.01$).
Figure 3A:
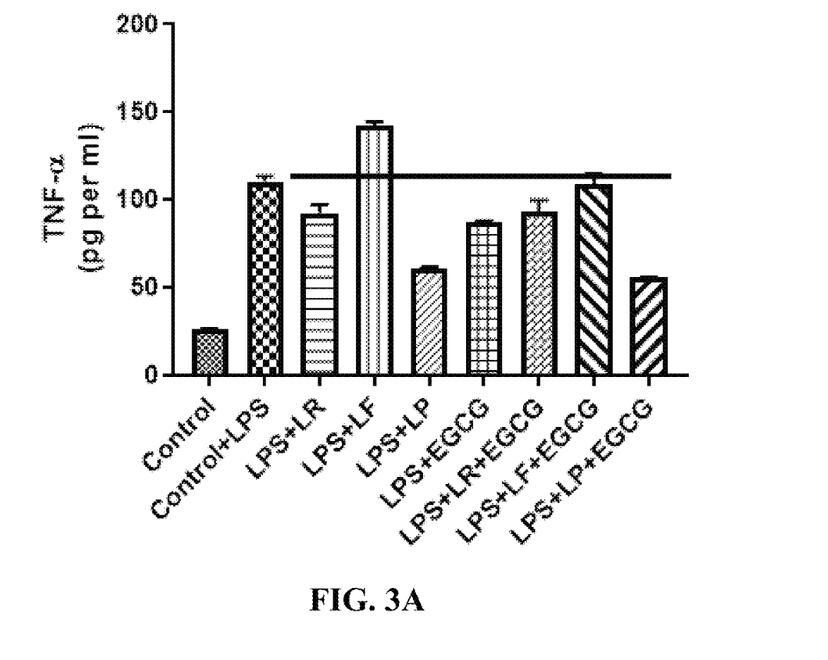
Figure 3B:
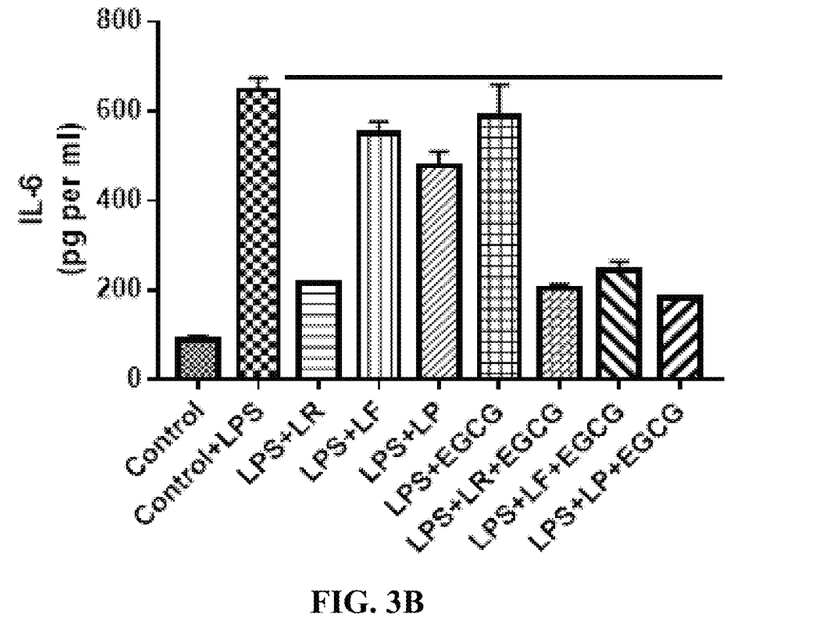
Figure 3C:
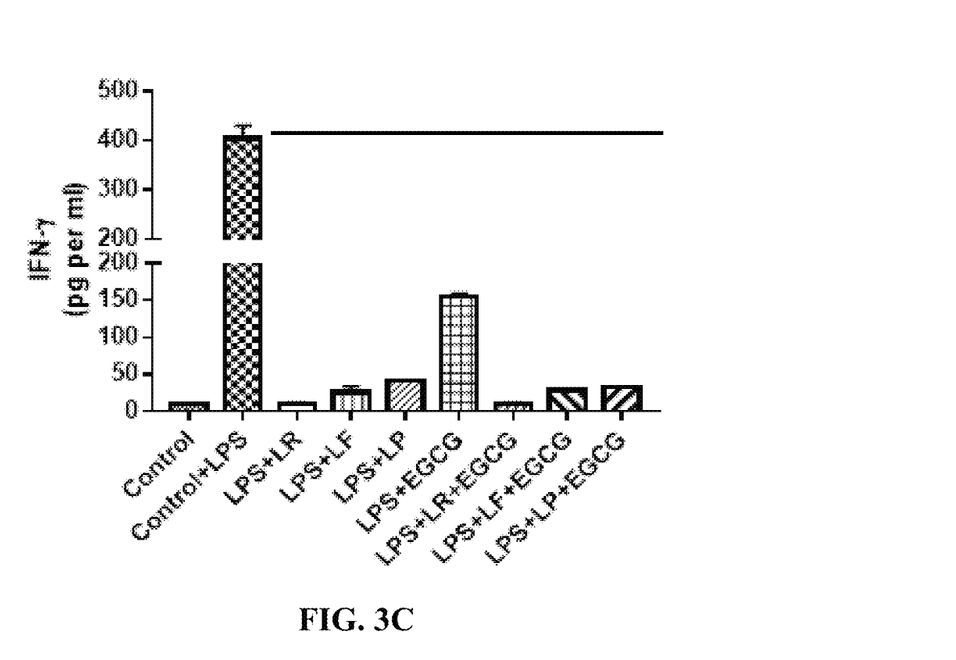

The synbiotic combinations of EGCG and probiotic species were tested for synergistic effects in amelioration of oxidative stress using tBHP in mice peripheral blood mononuclear cells (PBMCs). To prepare such a combination, EGCG was first isolated from fresh green shoots of *Kangra* green tea as previously described (Sharma et al. 2017). The probiotic bacteria were cultured in in de Man, Rogosa and Sharpe (MRS) broth (HiMedia laboratories, Mumbai-India) overnight and bacterial culture supernatant was collected after centrifugation. The pH of culture supernatant was adjusted to 6.8-7.0, sterile filtered, and mixed with RPMI-1640 5-20% v/v) to prepare final conditioned media. A synbiotic combination was formed by mixing EGCG (1-10 µM) and probiotic conditioned media (5-20% v/v) and applying to cells. The immune cells were specifically chosen as age-associated redox changes in immune cells affects not only their survival but also their functional capacity that ultimately is deleterious for the immune system rendering elderly prone to oxidative damage. Compared to the groups treated with probiotic alone or EGCG alone, a greater degree of change in the tested feature would be considered as a synergistic effect. It was observed that combination of EGCG and *Lactobacillus* sp (EGCG+LF) recorded minimum cell death in wake of oxidative stress as compared to either EGCG or bacterial treatment alone suggesting their protective effects on cell survival under stress (FIG. 2). The synbiotic combination of EGCG and probiotic species was further tested for synergistic effects in amelioration of inflammatory stress using bacterial lipopolysaccharide (LPS) in PBMCs of mice. Age-associated inflammatory stress (inflamm-aging) is a key process driving immunosenescence and organ damage. Analysis of inflammatory cytokines (IFN-γ/IL-6/TNF-α) revealed that while LPS induction produced strong inflammatory response, the combination of EGCG and *Lactobacillus* sp (EGCG+LF) recorded maximum inhibition of inflammation in wake of LPS induced stress as compared to either EGCG or bacterial treatment alone (FIG. 3). Together, it is reasonable to conclude that a combination of EGCG with LF displays synergistic attributes in preventing oxidative and inflammatory stress-induced cell death as compared to individual treatments of EGCG or LF. It thus shows that not only probiotic bacteria can survive in the presence of EGCG, but secretory metabolites of probiotics can synergistically enhance cell survivability with EGCG.

Example 3

Figure 4A:
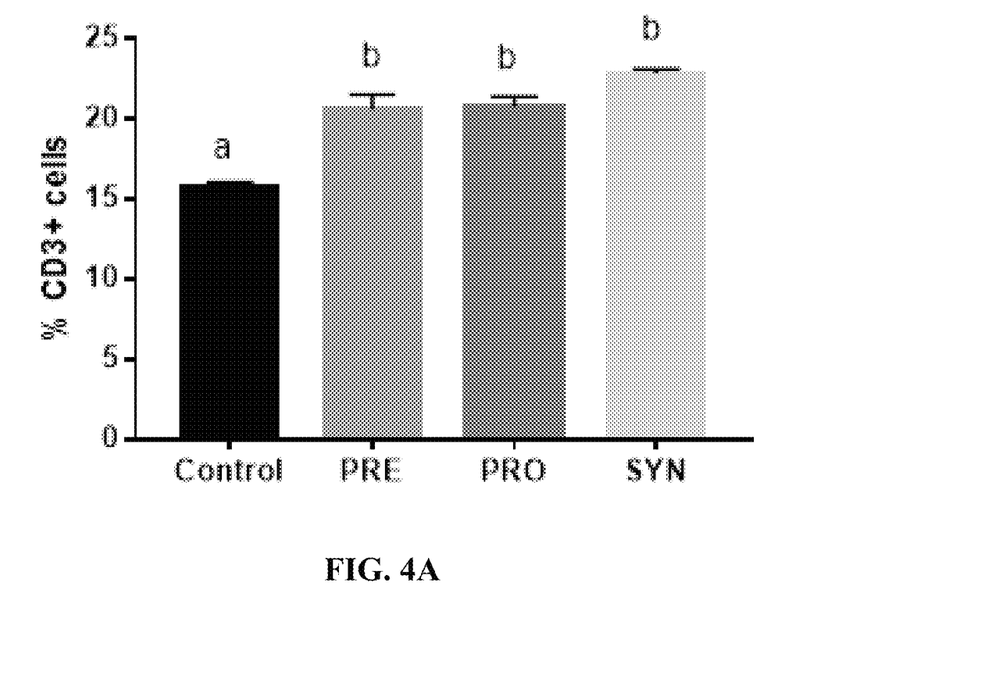
Figure 4B:
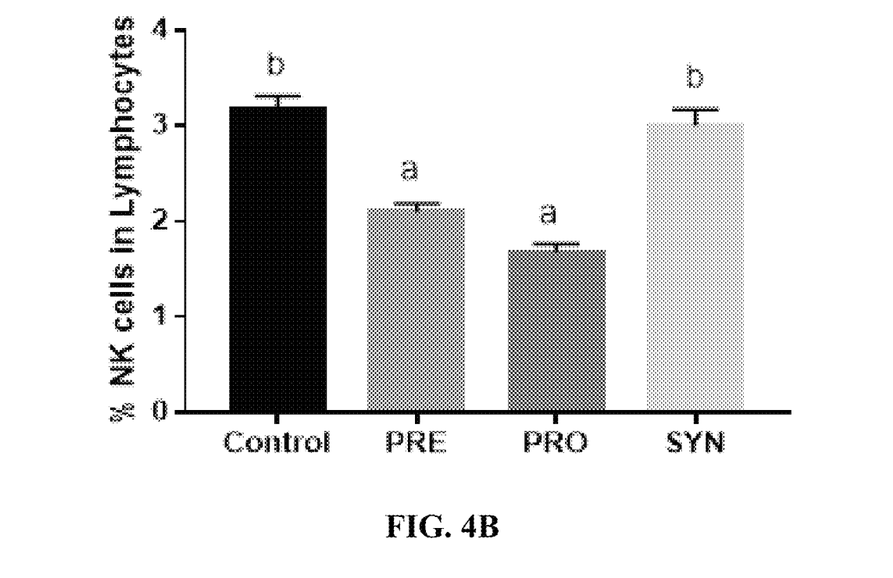
Figure 4C:
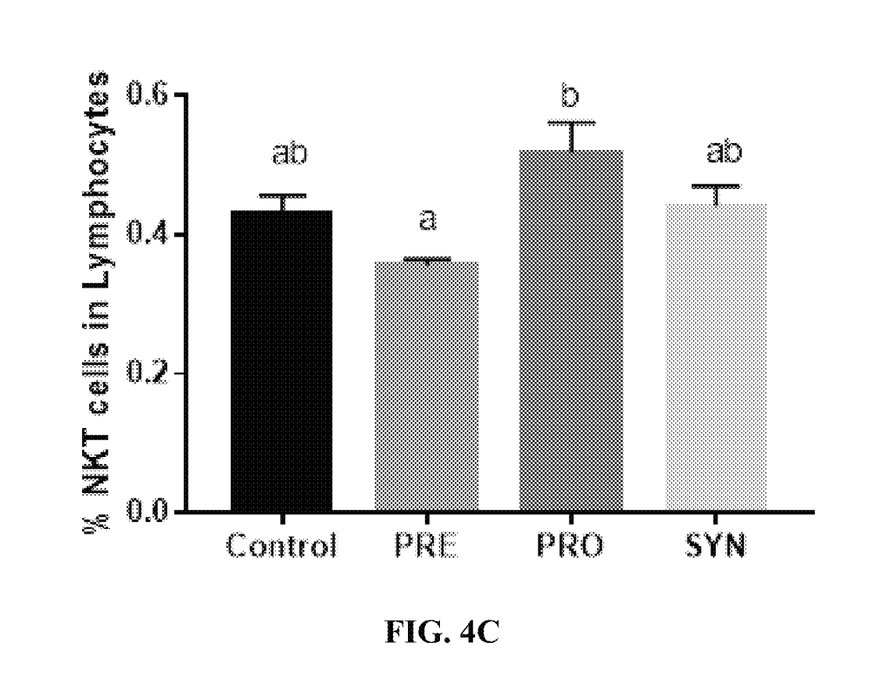
Figure 5A:
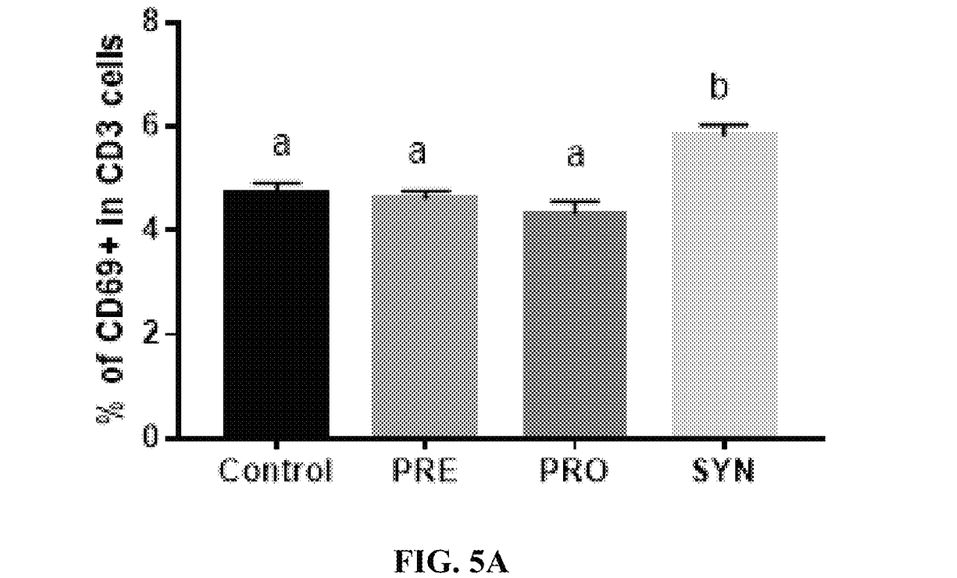
Figure 5B:
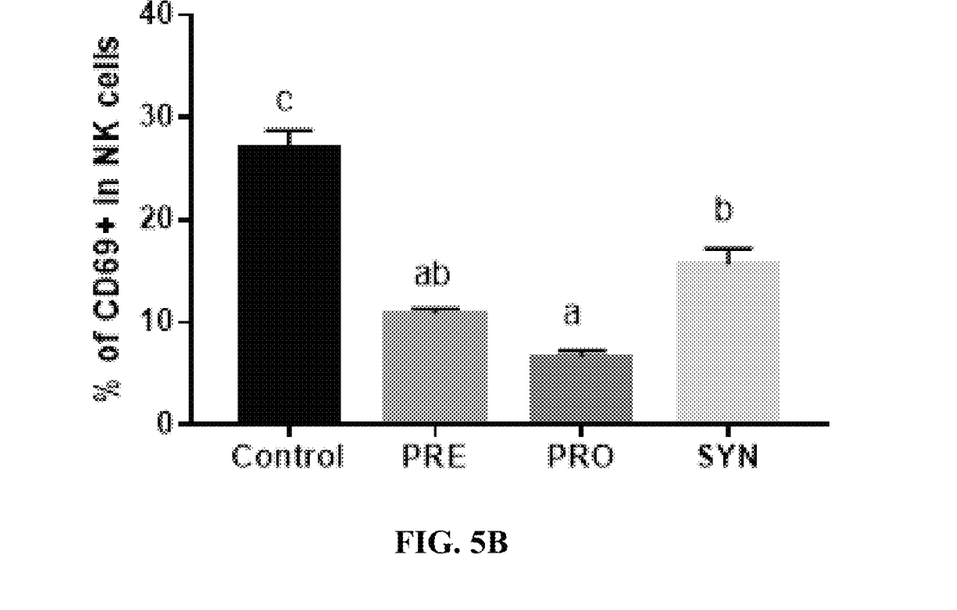
Figure 5C:
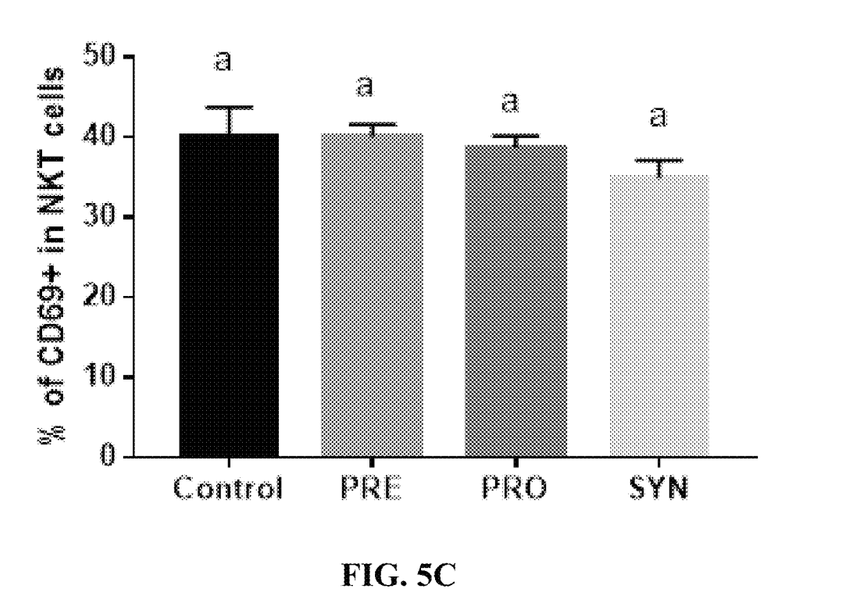

In Vivo Modulation of Cellular Immunity Using Synbiotic Composition in Aging Animals The synbiotic composition of EGCG and probiotic *Lactobacillus* sp was assessed for effects on cellular immune response using aging murine model. Animals (16 months old) were randomized into four groups of six mice each: 1 control group and 3 experimental groups comprising of either only EGCG (PRE), probiotic *Lactobacillus* sp (PRO) or a combination of both (SYN). All animals were fed on commercially available pelleted mice chow (Golden feeds, New Delhi, India) and water ad libitum. The experimental animal groups were each supplemented with EGCG (@100 mg/kg/animal/day), probiotic *Lactobacilli* sp ($10^8$ cfu/ml) or a combination of both above (synbiotic) respectively for 30 consecutive days. At the end of the feeding regimen, the animals were sacrificed for various immunological and antioxidative analysis. Flow cytometric analysis of splenocytes revealed significant changes in numbers and activation status of T-cells and subsets. The CD3+ T cells population reported an increase of up to 50% in all experimental groups as compared to control group (FIG. 4). Although the numbers of natural killer cells (NK) appeared to decrease in PRE and PRO fed groups as compared to control group; a significant increase in synbiotic fed group was observed while no significant difference in natural killer T cells (NKT) subpopulation could be observed (FIG. 4). However, the activation status (CD69) of CD3+ T cells reported a significant increase in synbiotic group only suggesting synergistic effects (FIG. 5). While no change in activation status of NKT cells could be observed, NK cells activation showed a pattern similar to those observed in their numbers. In particular, a decrease in activation of NK cells was observed in all treated groups (PRE/PRO/SYN) as compared to control group while no changes in activation status of NKT cells could be observed (FIG. 5). Decrease in numbers and inefficient immune response of T cells is considered a hallmark of immunosenescence and any interventions to revert this scenario would present a major anti-immunosenescence strategy. Therefore, an increase in proliferation as well as activation capacity of CD3+ T cells in synbiotic composition fed animals could greatly boost immune response and enhance their ability to resist and thwart off pathogenic infection. Although NK and NKT cells population and activation status was influenced by synbiotics as compared to individual treatments, however, no major change w.r.t control group could be observed. Increased NK cells activation and numbers have been reported with aging that may contribute to non-specific and exaggerated inflammatory response (inflamm-aging). In present invention, it appears that combination of PRE and PRO had a differential effect on proliferation and numbers of NK/NKT cells as opposed to their individual effects suggesting a classic example of synergy.

Figure 6A:
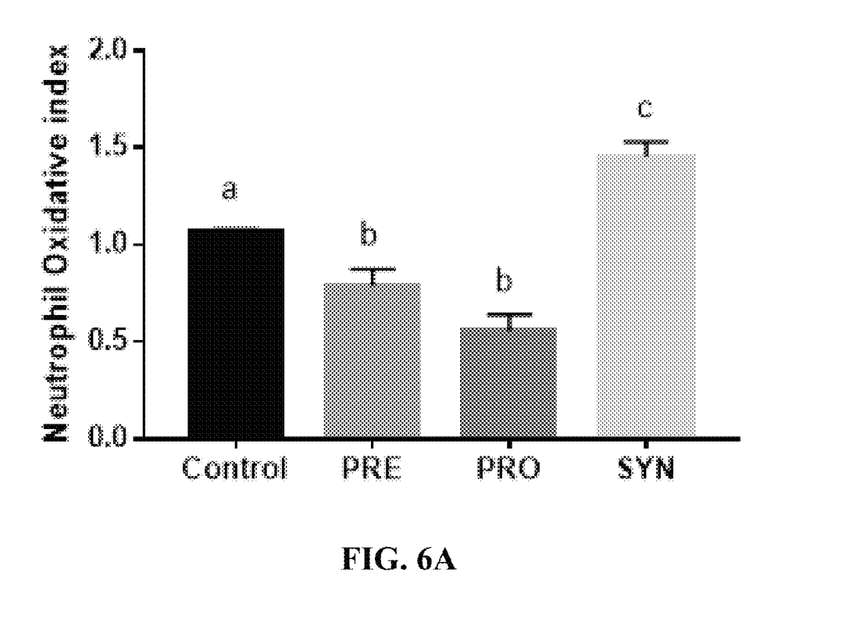
Figure 6B:
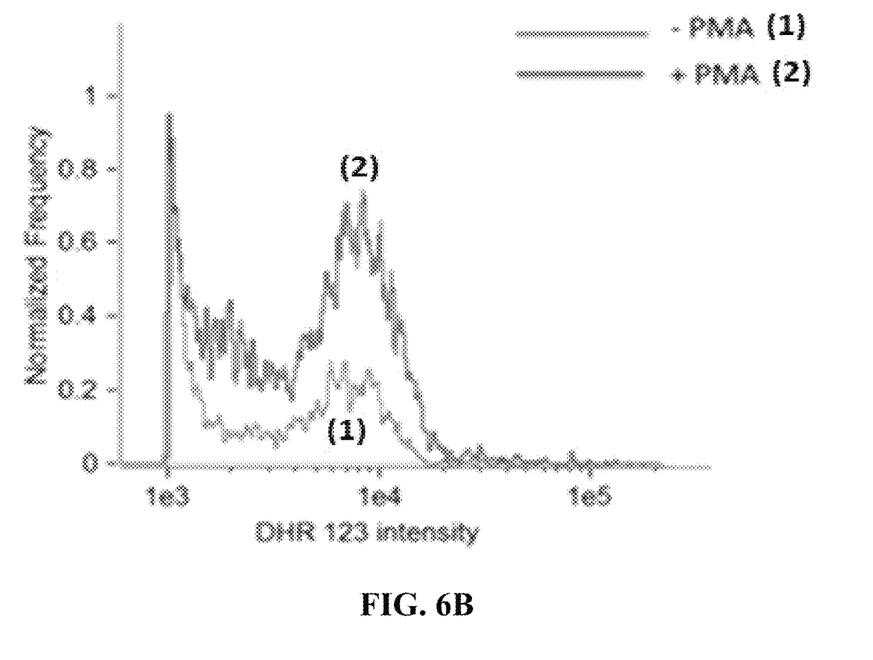
Figure 6C:
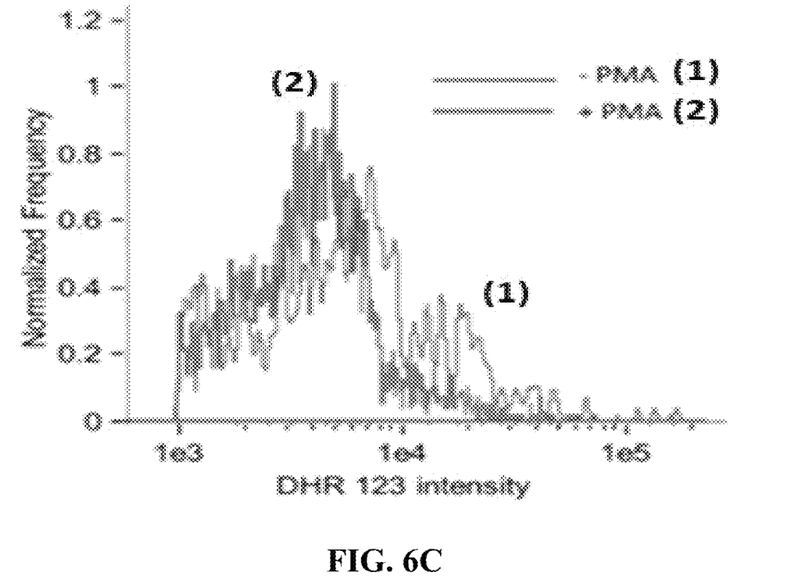
Figure 6D:
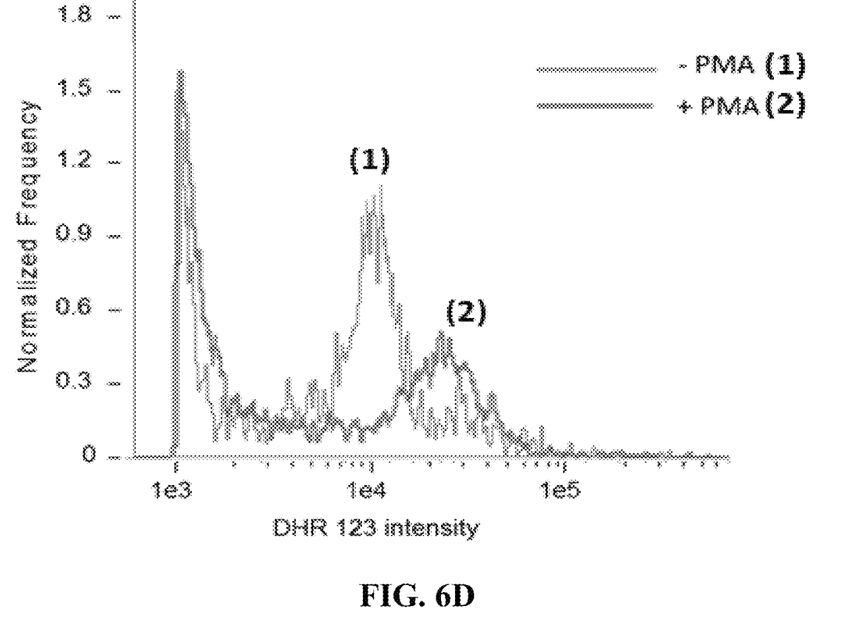
Figure 6E:
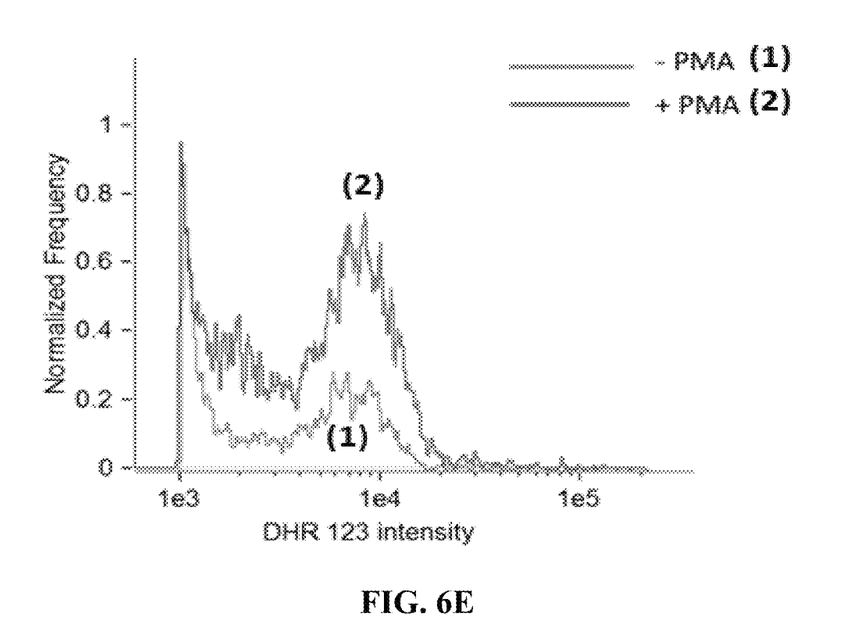

The effect of the synbiotic supplementation on the oxidative index of neutrophils is shown in FIG. 6a. Additionally, with continuing reference to FIG. 6, Representative Flow cytometry plots of different treatments of (B) Control (C) Prebiotic (D) Probiotic, and (E) Synbiotic are shown. Bars with different letters indicate significant difference at p<0.05.

Figure 7A:
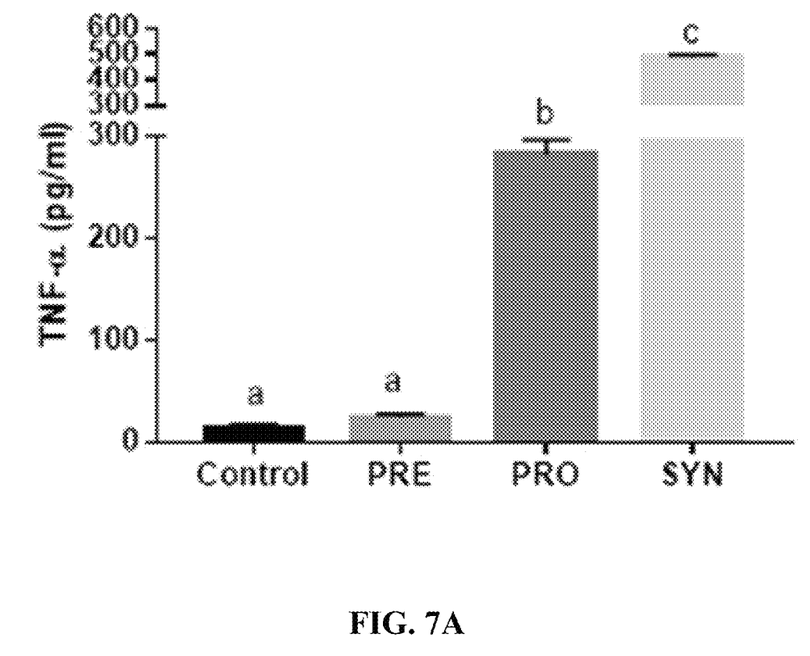
Figure 7B:
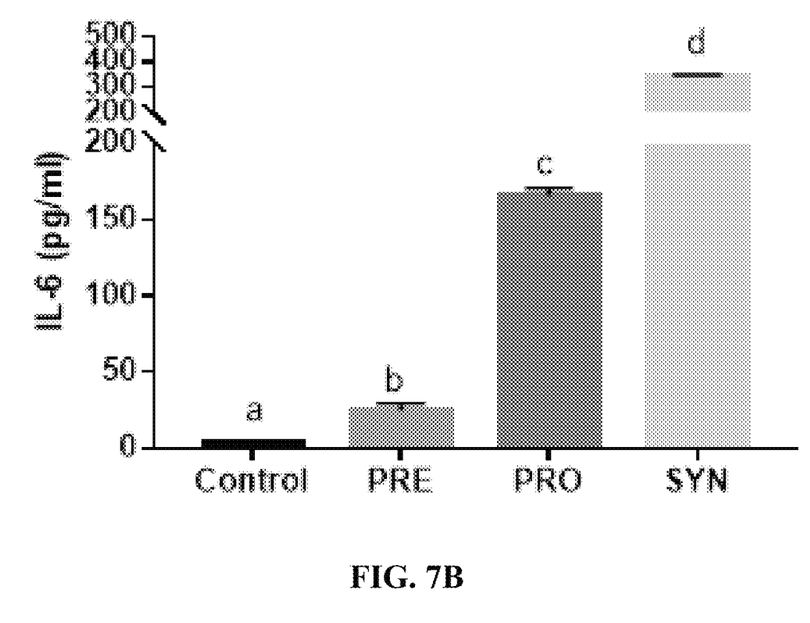
Figure 7C:
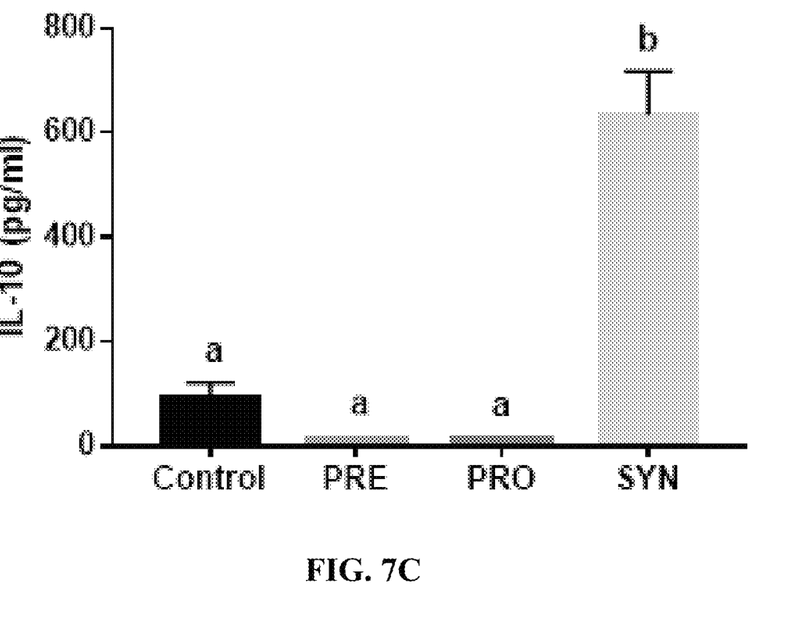

Functional analysis of peripheral blood neutrophils revealed that synbiotic treatment significantly enhanced oxidative index capacity of neutrophils on stimulation which was different to the observations recorded in individual treatments wherein a significant decrease w.r.t control group was observed (FIG. 7). This again signifies the synergistic aspect of the PRE-PRO combination.

The loss of neutrophil functions with aging both in murine and humans is well documented and is held accountable for impaired cellular immune response and recurring infections in elderly. Thus, supplementation with synbiotics appeared to significantly enhance neutrophil respiratory burst on that could be implicated in generation of a robust immune response on stimulation.

Example 4

Figure 8:
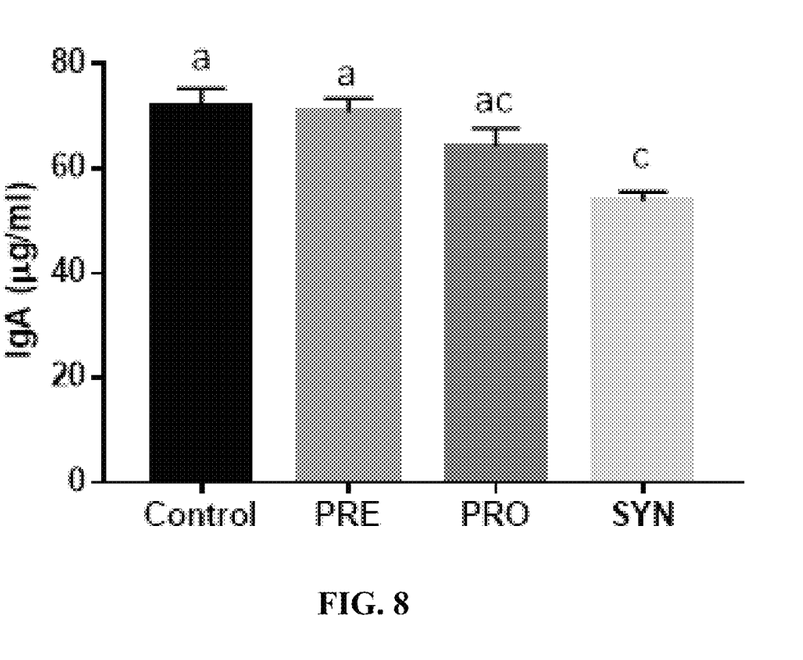
FIG. 8. Effect of synbiotic supplementation on immunoglobulin A production in intestinal fluid of aging animals. Bars with different letter indicate significant difference at $p<0.05$.

In Vivo Modulation of Functional Capacity of Immune Cells Using Synbiotic Composition in Aging Animals The cellular functions of immune cells were assessed on basis of production of cytokines, immunoglobulins and inflammatory homeostasis. Supplementation of the synbiotic composition had a profound effect on cytokines production in cultured splenocytes resulting in enhanced TNF-α, IL-6 and IL-10 production (multiple folds increase) (FIGS. 7A-7C). While probiotic supplementation only enhanced Th1 inflammatory response; supplementation of synbiotic composition enhanced both Th1 (TNF-α/IL-6) and Th2 (IL-10) cytokines (FIGS. 7A-7C). This is indicative of a greater control over immune homeostasis and ability to mount a robust immune response in wake of either pathogenic or allergic attacks in elderly on account of synbiotic supplementation. Further, to assess whether synbiotic treatment may have caused unwarranted systemic inflammation, NfkB activation status in liver of experimental animals was analyzed. Although, synbiotic composition enhanced inflammatory response in splenocytes, the NFKB expression recorded a significant decrease in all experimental groups as compared to control group. This suggests that treatment of synbiotic composition as well as individual components had an inhibitory effect on inflammation in liver and thus did not result in any over-activation of immune response that could otherwise be considered detrimental to organ functions. This is of significance as an age-associated increase in inflammation (inflamm-aging) is prevalent during aging that predisposes elderly to inflammatory disorders and infections. Thus, the bioactive components in the synbiotic composition could alleviate inflamm-aging while still activating immune system thereby help achieving an immune homeostasis. In addition, analysis of intestinal fluid revealed a significant decrease in IgA production in SYN group animals as compared to control group (FIG. 8). Although, supplementation of probiotics has been documented to enhance immunoglobulins response in gut, it is plausible to conclude that SYN treatment in present study influenced and activated cellular immune response in a major way as compared to humoral response that showed slight down-regulation.

Example 5

Figure 9:
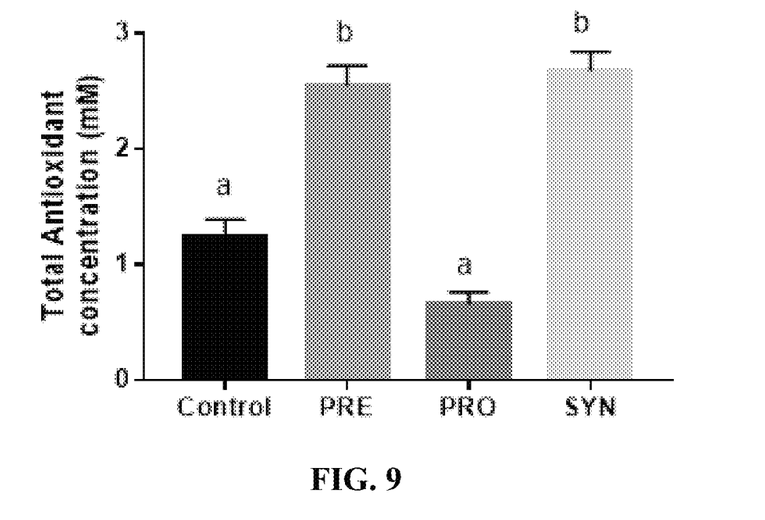
FIG. 9. Effect of synbiotic supplementation on total antioxidant capacity in plasma of aging animals. Bars with different letter indicate significant difference at $p<0.05$.
Figure 10A:
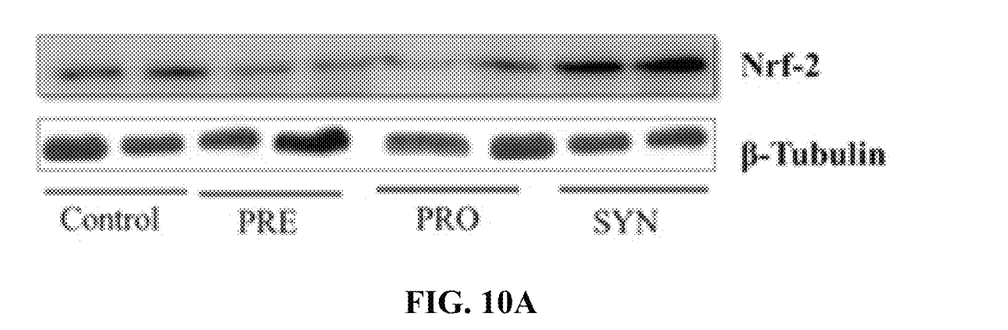
Figure 10B:
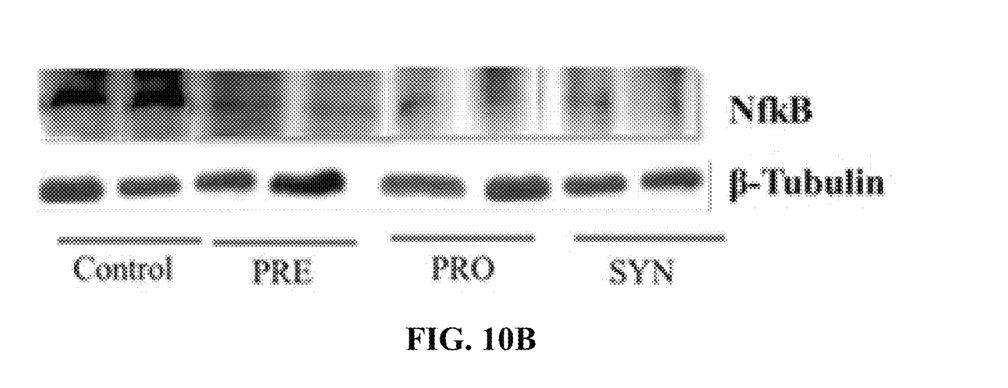

In Vivo Modulation of Antioxidant Capacity Using Synbiotic Composition in Aging Animals The synergistic effect of the synbiotic composition on antioxidant capacity of the aging animals was investigated. It was observed that the synbiotic composition improved the total antioxidant capacity in plasma as compared to probiotic alone suggesting robust antioxidative capacity in synbiotic fed animals (FIG. 9). Further assessment of nuclear factor erythroid 2-related factor 2 (Nrf2) revealed that synbiotic treatment in animals had significant increase in activation status of Nrf2 while no changes in the remaining groups could be observed (FIG. 10A). Once again, this emphasizes the synergistic effects of the SYN combination as opposed to individual treatments. The Nrf2 transcription factor controls the basal and induced expression of an array of antioxidant response element—dependent genes to regulate the physiological and pathophysiological outcomes of oxidant exposure. When Nrf2 is activated in the nucleus, it turns on the production of antioxidant enzymes such as catalase, glutathione and superoxide dismutase which would ultimately increase the antioxidant capacity of the cells as observed.

Advantages of the Invention

A composite mixture of bioactive molecule such as EGCG and a potent probiotic offers enhanced mutualistic as well as synbiotic benefits to the host as opposed to the effects exerted by individual components.

The developed synbiotic composition mitigated inflammatory and oxidative stress both in vitro and in vivo suggesting that the combination had age-associated stress ameliorating synergistic effects that greatly impacts cell functions during aging.

The developed synbiotic composition significantly influences the cellular immune response with increased numbers as well as activation status of CD3+ T cells that help in mitigating recurring infections in elderly.

The synergy of catechins and probiotic Lactobacilli enhances functional capacity of immune cells with a strong increase in Th1/Th2 cytokines production along with enhanced neutrophils respiratory burst suggesting robust immune activity in wake of either infection or allergic response.

The developed synbiotic composition did not result in any aggravation of inflammation and thus is useful in curbing inflamm-aging.

Synergy of catechins with probiotic *Lactobacilli* also beneficially alters the gut microbiome as catechins differentially influence bacterial growth.

The proposed synbiotic composition provides total catechins equivalent to drinking 4-cups of green tea in albeit a single drink/formulation that would be suitable for people who avoid green tea due to its astringent taste.

The invention claimed is:
1. A method of improving immune response and antioxidant capacity of an animal subject, the method comprising:
 administering a synbiotic composition to the animal subject, wherein the synbiotic composition comprises:
   (i) a probiotic micro-organism *Lactobacillus fermentum* MCC 3160, and
   (ii) a prebiotic epigallocatechin gallate (EGCG) isolated from Kangra green tea leaves from *Camellia sinensis*, wherein
improving immune response in the animal subject comprises an increase in the production of Th1 and Th2 cytokines, and
improving antioxidant capacity in the animal subject comprises activation of Nrf2 transcription factor.

2. The method of claim 1, wherein the synbiotic composition comprises a ratio of component (i):component (ii) ranging from 1:1 to 2:1.

3. The method of claim 1, wherein the synbiotic composition is administered in a dosage ranging from 6.66 to 10 mg/kg body weight of the animal subject.

4. The method of claim 1, wherein improving immune response in the animal subject further comprises a modulation of cellular immune response with an increase in the number of CD3+ T cells and enhanced activation of CD3+ T cells and neutrophils.

5. The method of claim 1, wherein the composition is administered to the animal subject in a food composition.

6. The method of claim 5, wherein the food composition further comprises nutrients selected from the group consisting of minerals, vitamins, amino acids, unsaturated fatty acids, polyphenols, plant sterols and mixtures thereof.

7. The method of claim 1, wherein the composition is administered to the animal subject in a milk-based formulation.

8. The method of claim 7, wherein the milk-based formulation further comprises nutrients selected from the group consisting of minerals, vitamins, amino acids, unsaturated fatty acids, polyphenols, plant sterols and mixtures thereof.

9. The method of claim 1, wherein the synbiotic composition comprises $10^8$ to $10^9$ CFU of the probiotic microorganism *Lactobacillus fermentum* MCC 3160 and 400 to 500 mg of the prebiotic EGCG.

* * * * *